United States Patent [19]

Podos et al.

[11] Patent Number: 4,490,379

[45] Date of Patent: Dec. 25, 1984

[54] METHOD OF REDUCING INTRAOCULAR PRESSURE AND TREATING GLAUCOMA USING CORYNANTHINE

[76] Inventors: Steven Podos, 2 Knoll Rd., Tenafly, N.J. 07670; Janet B. Serle, 1249 Park Ave., New York, N.Y. 10029; Thomas Mittag, 167 Woodland Dr., Pleasantville, N.Y. 10570

[21] Appl. No.: 596,533

[22] Filed: Apr. 4, 1984

[51] Int. Cl.³ .......................................... A61K 31/475
[52] U.S. Cl. .................................................... 424/262
[58] Field of Search ........................................ 424/262

[56] References Cited

PUBLICATIONS

Chem. Abst. 100(21): 168109z (1984)–Doxey et al.

*Primary Examiner*—Douglas W. Robinson
*Attorney, Agent, or Firm*—Brumbaugh, Graves, Donohue & Raymond

[57] ABSTRACT

This invention relates to a method of reducing intraocular pressure and treating glaucoma in mammals which comprises administering topically to the eye a pharmaceutically acceptable salt isomeric to yohimbine and stereochemically similar to corynanthine in an amount effective to reduce intraocular pressure.

6 Claims, No Drawings

METHOD OF REDUCING INTRAOCULAR PRESSURE AND TREATING GLAUCOMA USING CORYNANTHINE

BACKGROUND OF THE INVENTION

1. Field of the Invention

This invention relates to a method of lowering intraocular pressure and treating glaucoma in mammals using corynanthine and compounds related to corynanthine and particularly to the topical application of these compounds to the eye of mammals in order to lower the intraocular pressure caused by glaucoma.

Glaucoma refers to a group of diseases of the eye which are characterized by abnormally high intraocular pressure. The outer shell of the eyeball is made up of three coats. A tough outer fibrous tunic composed of variously arranged connective tissue fibers, the uveal tunic and the retina. The choroid is the posterior segment of the uveal tunic. The anterior part of the uvea, in part, is referred to as the ciliary body and is lined with two epithelial cell layers which secrete the aqueous humor which fills the anterior chamber of the eye. In a healthy eye the humor flows from the ciliary body through the pupil into the anterior chamber of the eye and leaves the eye through Schlemm's canal. The rate of formation and the rate of exit of this aqueous humor determines the intraocular pressure in the eyeball.

In subjects suffering from glaucoma the rate of elimination of aqueous humor from the eye is reduced which results in fluid build up within the eye and increased intraocular pressure. If high intraocular pressure is allowed to continue untreated it interferes with the blood supply to the nerve fibers of the retina and optic nerve and if left uncorrected the optic nerve dies and blindness results.

Glaucoma can be treated both through surgery or therapeutically with drugs. Surgery seeks to create new outlets for the aqueous humor and thereby reduce the intraocular pressure. A number of drugs have been discovered which when either taken internally or applied topically to the eye lower intraocular pressure but many are toxic and cause undesirable side effects, especially when used as chronic therapy.

2. Description of the Prior Art

Adrenergic agents have been explored for the treatment of chronic open-angle glaucoma. Epinephrine, a nonspecific $\alpha$ and $\beta$ adreneric agonist, and Timoptic, a $\beta$ adrenergic antagonist are currently used clinically for the treatment of glaucoma. Other drugs with predominantly $\alpha$ adrenergic antagonist receptor specificity, such as prazosin and thymoxamine, have been examined with respect to their effect on intraocular pressure. Prazosin and thymoxamine successfully reduce intraocular pressure in rabbits. Neither drug however has been effective in reducing intraocular pressure in humans.

The present treatment of open-angle glaucoma is limited to four types of pharmacologic agents: (1) the topically applied cholinergic agents, pilocarpine, carbachol, and phospholine iodide, (2) the topically applied but nonselective $\alpha$ and $\beta$ adrenergic agonist, epinephrine, (3) the topically applied $\beta$ adrenergic antagonist, timolol, and (4) the systemically administered carbonic anhydrase inhibitors acetazolamide and methazolamide. There is currently a need for more effective and selective adrenergic agents for the treatment of glaucoma to eliminate undesirable side effects of the presently employed drugs, and to widen the range of therapeutic choices.

The effects of $\alpha$ adrenergic agents on aqueous humor dynamics have been studied in several different species. Some of the drugs that have been investigated have different effects on ocular aqueous humor parameters in different species. Varying responses to the same drug have been found which is perhaps due to differences in adrenergic receptor quantity, location and regulation amongst the species.

Innemee et al. in a paper entitled Differential Effects of Selective $\alpha_1$ and $\alpha_2$ Adrenoceptor Agonists on Intraocular Pressure in the Conscious Rabbit. Doc Ophthalmol 52:287, 1982 recently studied the effects of selective $\alpha_1$ and $\alpha_2$ adrenergic agonists on intraocular pressure in rabbits. They demonstrated that the topical application of the selective $\alpha_1$ agonists, phenylephrine and St 587, caused an initial elevation in intraocular pressure, followed by a fall in pressure below baseline values. Topical application of the selective $\alpha_2$ agonist B-HT 920 resulted in a prolonged ocular hypotensive effect. However, Lee and Brubaker in "Effect of Phenylephrine on Aqueous Humor Flow", Curr Eye Res 2:89, 1982 demonstrated that phenylephrine had no effect on intraocular pressure or aqueous humor secretion in man.

Clonidine is a nonselective $\alpha_1$ and $\alpha_2$ adrenergic agonist. It is known to reduce intraocular pressure in humans and monkeys, but raises intraocular pressure in rabbits. It has no effect on outflow facility or aqueous humor flow rates in monkeys, and no effect on outflow facility in humans, Hodapp E, et al.: The Effect of Topical Clonidine on Intraocular Pressure, Arch Ophthalmol 99:1208, 1981; Bill A, Heilmann K: Ocular Effects on Clonidine in Cats and Monkeys (macaca irus), Exp Eye Res 21:481, 1975; Krieglstein GK, et al.: The Peripheral and Central Neural Actions of Clonidine in Normal and Glaucomatous Eyes, Invest Ophthalmol Vis Sci 17:149, 1978. Norepinephrine, a nonselective $\alpha$ agonist, lowers intraocular pressure in rabbits, by increasing outflow facility and reducing aqueous humor flow, Green K, Padgett D: Effect of Various Drugs on Pseudofacility and Aqueous Humor Formation in the Rabbit Eye, Exp Eye Res 28:239, 1979. It has no effect on intraocular pressure, outflow facility or aqueous humor flow rates in monkeys, Bill A: Effects of Norepinephrine, Isoproterenol and Sympathetic Stimulation on Aqoueous Humor Dynamics in Vervet Monkeys, Exp Eye Res 10:31, 1970. Epinephrine, a nonselective $\alpha$ and $\beta$ agonist, reduces intraocular pressure in rabbits and humans, Langham ME, Krieglstein GK: The Biphasic Intraocular Pressure Response of Rabbits to Epinephrine, Invest Ophthalmol Vis Sci 15:119, 1976; Townsend DJ, Brubaker RF: Immediate Effect of Epinephrine on Aqueous Formation in the Normal Human Eye as Measured by Fluorophotometry, Invest Ophthalmol Vis Sci 19:256, 1980. It causes an initial increase in intraocular pressure in monkeys, Bill A: Early Effects on Epinephrine on Aqueous Humor Dynamics in Vervet Monkeys (cercopithecus ethiops), Exp Eye Res 8:35, 1969. It increases outflow facility in all three species, reduces aqueous humor flow rates in rabbits, increases aqueous flow in humans and has no effect on aqueous humor flow in monkeys, Lorenzetti OJ: Dose-Dependent Influence of Topically Instilled Adrenergic Agents on Intraocular Pressure and Outflow Facility in the Rabbit, Exp Eye Res 12:80, 1971; Barany EH: Topical Epinephrine Effects on True Outflow Resistance and Pseudofacility in Vervet Monkeys Studied by a New Anterior Chamber Perfusion Technique, Invest Ophthalmol Vis Sci 7:88, 1968.

Thymoxamine, a relatively nonselective α adrenergic antagonist has no effect on intraocular pressure, outflow facility or aqueous humor flow rates in humans but reduced intraocular pressure in rabbits, Lee DA, et al.: Effect of Thymoxamine on Aqueous Humor Formation in the Normal Human Eye as Measured by Fluorophotometry, Invest Ophthalmol Vis Sci 21:805, 1981; Sobel LI, et al.: Adrenergic Receptors in Rabbit Iris-ciliary Body Quantitation of the Alpha-2 Subtype, Invest Ophthalmol Vis Sci, Suppl 24:89, 1983. Nylidrin, a selective $\alpha_1$ antagonist and nonselective β agonist, lowers intraocular pressure in all three species, Sobel L, et al.: Topical Nylidrin and Aqueous Humor Dynamics in Rabbits and Monkeys, Arch Ophthalmol (in press); Bucci MG: Effects of New Topical β-mimetic (isoxuprine and nylidrin) and β-lytic (oxprenolol) Agents on the Ocular Pressure in Glaucomatous eyes, Ophthalmol Res 9:238, 1977. It has no effect on outflow facility or aqueous humor flow rates in monkeys and rabbits. Prazosin, a selective $\alpha_1$ antagonist, reduces intraocular pressure in rabbits, without changing outflow facility, Rowland JM, Potter DE: The Effects of Topical Prazosin on Normal and Elevated Intraocular Pressure and Blood Pressure in Rabbits, Eur J Pharmacol 64:361, 1980; Krupin T, et al.: Effect of Prazosin on Aqueous Humor Dynamics in Rabbits, Arch Ophthalmol 98:1639, 1980. Posterior chamber ascorbate measurements indicate prazosin also reduces aqueous flow rates in rabbits.

DISCLOSURE OF THE INVENTION

It is the object of this invention to find a new method of lowering intraocular pressure in mammals. It has now been discovered that topical applications of corynanthine, a selective $\alpha_1$ adrenergic receptor antagonist, significantly (p<0.05) lowers intraocular pressure (mean mm Hg±SEM) in mammals including man. No local ocular or systemic side effects have been observed after the topical application of corynanthine.

Corynanthine is one of ten naturally occurring or synthetically prepared stereoisomers of the following structure which is related to yohimbine:

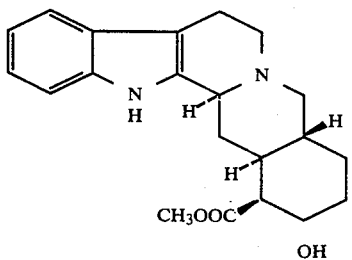

The adrenergic properties and the α adrenergic receptor selectivity of yohimbine and its stereoisomers have been clearly demonstrated in the literature. These studies indicate that yohimbine selectively blocks $\alpha_2$ adrenergic receptor sites and the corynanthine isomer preferentially blocks $\alpha_1$ receptor sites.

Corynanthine tartrate (Sigma Chemical Co., St. Louis, Mo) has been tested and found useful in lowering intraocular pressure in rabbits, monkeys and humans but it is believed that any pharmaceutically acceptable salt of corynanthine or compounds isomeric to yohimbine and stereochemically similar to corynanthine would also be effective.

The corynanthine compound can be applied topically to the eye of a mammal in any pharmaceutically accepted manner including but not limited to sterile ophthalmic solutions, ointments, subconjunctival injections, and slow release devices. In addition to the active corynanthine compound, a pharmaceutical composition can contain among other things pharmaceutically acceptable preservatives, antioxidants, viscosity vehicles, stabilizers and buffers.

Corynanthine differs from the currently used types of antiglaucoma agents, in that it is a selective α adrenergic antagonist. Corynanthine will provide a new topical antiglaucoma drug. It will defer the use for the treatment of glaucoma of known systemic agents which have greater side effects than the topical agents. Corynanthine will also provide an alternative to topical medications that are contraindicated in select patient groups, such as asthmatics, and cardiac patients since known β adrenergic antagonists pose a potential risk for these patients.

An additional risk of β-blockers is their potential for retinal toxicity which may not be present in an α antagonist such as corynanthine. Corynanthine may be more effective than the topical medications presently available and it may replace some of the topical agents currently used, or it may decrease the number of antiglaucoma medications an individual must use to keep his intraocular pressure under control.

In addition to treating open-angle glaucoma, corynanthine may also be useful in the treatment of narrow-angle glaucoma. Corynanthine, like pilocarpine, is a miotic. In contrast to pilocarpine however, corynanthine does not affect accommodation. Moreover, corynanthine, unlike pilocarpine will not cause an attack of narrow-angle glaucoma due to anterior displacement of the lens iris diaphragm.

DESCRIPTION OF PREFERRED EMBODIMENT

The invention will be more clearly understood by reference to the following examples which are given by way of illustration and are not meant to limit the invention in any way.

I. ANIMAL TESTS

Example 1

Intraocular pressure was measured using a manometrically calibrated pneumatonograph in three groups of adult, restrained, albino rabbits weighing between 2 and 3 kg. One to two drops of 0.5% topical proparacaine hydrochloride anesthesia was instilled prior to all measurements. Intraocular pressure measurements were obtained prior to the topical application of the corynanthine tartrate, and 30, 60, 120, 240 and 360 minutes after drug application. Corynanthine tartrate (Sigma Chemical Co., St. Louis, Mo.) was prepared in distilled water in 1%, 2% and 5% solutions, at a neutral pH. Distilled water was used as the control. One drop of 50 ul of corynanthine tartrate was applied randomly to one eye and distilled water of equal volume to the contralateral eye.

The 5% corynanthine solution significantly (p<0.05) lowered intraocular pressure in rabbits for at least six hours (Table 1). Baseline intraocular pressure measurements were similar in treated and control eyes. The maximum significant (p<0.005) reduction in intraocular pressure, comparing treated and control eyes, occurred 30 minutes after drug administration; intraocular pressure was 12.6±0.9 mm Hg (mean±SEM) in the treated eye, compared to 15.9±0.4 mm Hg in the control eye. The 2% corynanthine solution significantly ($p<0.05$) reduced intraocular pressure for four hours. Baseline intraocular pressure measurements were similar in both eyes. The maximum significant ($p<0.005$) reduction in intraocular pressure, comparing treated and control eyes, occurred 60 minutes after drug application. The 1% corynanthine solution significantly ($p<0.005$) reduced intraocular pressure at 120 minutes. There was no significant change in intraocular pressure in the control eyes of these three groups of rabbits.

TABLE 1

Effect of Corynanthine Tartrate on Intraocular Pressure in Rabbits

| Concentration | No. | Mean Intraocular Pressure + SEM (mm Hg) | | | | | |
|---|---|---|---|---|---|---|---|
| | | Base | 30 min | 60 min | 120 min | 240 min | 360 min |
| 1% | 8 | 14.5 ±0.5 | 13.4 ±0.9 | 12.8 ±0.6 | 12.5** ±0.7 | 15.0 ±0.7 | 15.9 ±0.5 |
| Diluent | | 14.8 ±0.5 | 14.6 ±0.6 | 14.4 ±0.9 | 14.5 ±0.5 | 15.4 ±0.6 | 16.0 ±0.5 |
| 2% | 8 | 16.1 ±0.3 | 12.8* ±0.8 | 11.3** ±0.9 | 11.4* ±1.0 | 12.1* ±1.1 | 14.1 ±0.7 |
| Diluent | | 15.6 ±0.3 | 15.5 ±0.4 | 14.4 ±0.7 | 13.4 ±1.0 | 13.9 ±0.7 | 14.6 ±0.6 |
| 5% | 8 | 17.1 ±0.3 | 12.6** ±0.9 | 12.9** ±1.0 | 12.5* ±0.9 | 13.5* ±0.8 | 16.1* ±0.6 |
| Diluent | | 16.8 ±0.4 | 15.9 ±0.4 | 15.6 ±0.6 | 13.8 ±0.8 | 14.8 ±0.4 | 17.6 ±0.4 |

*Significant difference between treated and control eyes, ($p < 0.05$).
**Significant difference between treated and control eyes, ($p < 0.005$).

Example 2

Adult cynomolgus monkeys, weighing between 4 and 5 kg, were used to evaluate the effect of corynanthine tartrate on intraocular pressure, outflow facility and aqueous humor flow rates. All primate experiments were conducted using 5% corynanthine tartrate solution, prepared as described in Example 1. One 50 ul drop of the drug was randomly, topically, unilaterally administered. Distilled water of equal volume was used as the control.

Intraocular pressures were measured using a manometrically calibrated pneumatonograph on ten awake monkeys. The monkeys were restrained in a sitting position in specially designed chairs, and trained to cooperate during pressure measurements. Topical 0.5% proparacaine hydrochloride anesthesia was instilled prior to all intraocular pressure measurements. Baseline intraocular pressure measurements were taken prior to the topical application of corynanthine tartrate, and 30, 60, 90, 120, 240 and 360 minutes after drug administration. After a two week wash-out period, the same intraocular pressure measurement protocol was repeated on ten monkeys anesthetized with ketamine (3 mg/kg intramuscular).

Intraocular pressure was significantly ($p<0.02$) reduced for at least six hours in the ten awake cynomolgus monkeys tested (Table 2). Baseline intraocular pressure measurements were similar in treated and control eyes. The maximum significant ($p<0.005$) reduction in intraocular pressure, comparing treated and control eyes, occurred 120 minutes after drug administration; intraocular pressure 12.7±0.5 mm Hg in the treated eyes, and 15.9±0.4 mm Hg in the control eyes. The ten monkeys anesthetized with ketamine had a significant ($p<0.02$) reduction in intraocular pressure for four hours after drug administration. The maximum significant ($p<0.005$) reduction in intraocular pressure occurred 120 minutes after drug administration. Intraocular pressure was 12.9±0.8 mm Hg in treated eyes and 15.1±0.6 mm Hg in control eyes. There was no significant change in the intraocular pressure in the control eyes of the monkeys.

Slit lamp examination revealed the anterior chambers to be quiet throughout the experiment. No conjunctival injection was observed in the monkeys or the rabbits.

TABLE 2

Effect of 5% Corynanthine Tartrate on Intraocular Pressure in Monkeys

| | No. | Mean Intraocular Pressure + SEM (mm Hg) | | | | | |
|---|---|---|---|---|---|---|---|
| | | Base | 30 min | 60 min | 120 min | 240 min | 360 min |
| Awake | | | | | | | |
| Treated | 10 | 15.8 ±0.5 | 14.7* ±0.6 | 13.2** ±0.5 | 12.7** ±0.5 | 13.9* ±0.5 | 15.0* ±0.3 |
| Diluent | | 16.0 ±0.4 | 15.5 ±0.6 | 15.2 ±0.3 | 15.9 ±0.4 | 15.9 ±0.3 | 16.3 ±0.3 |
| Anesthetized | | | | | | | |
| Treated | 10 | 16.2 ±0.6 | 15.9 ±0.8 | 14.3* ±1.0 | 12.9** ±0.8 | 14.2* ±0.8 | 14.7 ±1.1 |
| Diluent | | 16.2 ±0.6 | 15.9 ±0.7 | 15.5 ±0.7 | 15.1 ±0.6 | 15.5 ±0.7 | 15.5 ±0.9 |

*Significant difference between treated and control eyes, ($p < 0.02$).
**Significant difference between treated and control eyes, ($p < 0.005$).

Example 3

Outflow facility was measured using an electronic tonometer on eleven monkeys anesthetized with ketamine, (3 mg/kg intramuscular). Topical 0.5% proparacaine hydrochloride anesthesia was used prior to all tonographic measurements. Tonography was performed two hours before, and two hours after the topical administration of corynanthine tartrate.

Tonograms performed on eleven monkeys confirmed a significant ($p<0.001$) reduction in intraocular pressure in treated eyes compared to control eyes two hours after 5% corynanthine tartrate application. There was no significant ($p<0.30$) change in intraocular pressure in control eyes before and after treatment. There was no significant ($p<0.10$) difference in measured outflow facility between treated and control eyes, prior to or after drug administration.

TABLE 3

Effect of 5% Corynanthine Tartrate on Outflow Facility in 11 Monkeys Anesthetized with Ketamine

| | Mean Outflow Facility + SEM (ul/min/Hg) | |
|---|---|---|
| | Base | 120 min |
| Treated | 0.52 ±0.04 | 0.55 ±0.03 |
| Diluent | 0.52 ±0.04 | 0.46 ±0.03 |

Example 4

Aqueous humor flow rates were determined on twelve cynomolgus monkeys using a slit lamp fluorophotometer, Schenker HI, et al.: Fluorophotometric Study on Epinephrine and Timolol in Human Subjects, Arch Ophthalmol 99:1212, 1981. The animals were anesthetized with ketamine (3 mg/kg intramuscular) prior to iontophoresis and prior to measurements of fluorescein concentration in the cornea and the anterior chamber. Topical 0.5% proparacaine hydrochloride anesthesia was installed bilaterally; 10% fluorescein solution in 2% agar gel was then iontophoretically applied to the central cornea for 5 min. at least 14 hours before fluorophotometric measurements were begun. Four to five readings were taken at 30 minute intervals to establish baseline flow rates prior to drug application. Corynanthine tartrate was applied randomly to one eye and distilled water to the contralateral eye. Readings were then taken 30, 60, 90, 120 and 180 minutes after drug administration. The fluorophotometric apparatus was standardized prior to, and subsequent to, each reading using a reference fluorescent glass. Calculations of the aqueous humor flow rate, F, and the anterior chamber elimination coefficient, Ko, were made using the model of Jones and Maurice Jones RF, Maurice DM: New methods of Measuring the Rate of Aqueous Flow in Man with Fluorescein, Exp Eye Res 5:208, 1966. For these calculations, we assumed a cornea volume of 50 ul, and an anterior chamber volume of 108 ul.

Fluorophotometrically measured baseline aqueous humor flow rates were similar in the treated and control eyes of the twelve cynomolgus monkeys tested (Table 4). Corynanthine did not significantly ($p<0.30$) alter aqueous humor flow rates in the treated and control eyes for 180 minutes after application. Ko, the anterior chamber elimination coefficient was $0.0133\pm0.0008$ min$^{-1}$ (mean±SEM).

TABLE 4

Effect of 5% Corynanthine Tartrate on Aqueous Humor Flow Rates as Measured by Fluorophotometry in 12 Monkeys Anesthetized with Ketamine

| | Aqueous Humor Flow + SEM (ul/min) | | | | | |
|---|---|---|---|---|---|---|
| | Base | 30 min | 60 min | 120 min | 240 min | 360 min |
| Treated | 1.6 ±0.2 | 1.1 ±0.1 | 1.3 ±0.3 | 1.4 ±0.3 | 1.5 ±0.4 | 1.5 ±0.2 |
| Diluent | 1.5 ±0.2 | 1.3 ±0.3 | 1.1 ±0.3 | 1.5 ±0.3 | 1.3 ±0.2 | 1.1 ±0.2 |

Example 5

The pupillary diameter was measured on six monkeys, using a clear ruler. Measurements were taken under standard illumination to the nearest 0.5 mm prior to, 30, 60, 120, 240 and 360 minutes after corynanthine application.

Corynanthine caused a significant ($p<0.05$) unilateral miosis in six monkeys for four hours. Prior to drug application, pupil diameter was $5.3\pm0.4$ mm (mean±SEM) in both treated and control eyes. At 30 minutes the diameter was $4.5\pm0.2$ mm in the treated eyes, compared to $5.5\pm0.5$ mm in the control eyes. At four hours, the pupils in the treated eyes measured $3.8\pm0.3$ mm and the control eyes $5.0\pm0.4$ mm. At six hours, the difference in pupil diameter between treated and control eyes was not significant.

All results reported in Examples 1–5 were analyzed for the treated and contralateral control eyes. The paired t-test was used to compare the two eyes in a single experiment. The Student t-test was used for intergroup analysis.

II. HUMAN TESTS

Example 6

The effects of corynanthine on intraocular pressure, anterior chamber depth, pupil size, blood pressure and pulse rate were studied in ten patients with ocular hypertension. Corynanthine tartrate was applied topically in 1%, 2% and 5% sterile distilled water solutions in a randomized, double blind fashion. The above parameters were measured hourly for eight hours.

The topical application of the 2% solution significantly ($p<0.05$) reduced intraocular pressure for at least eight hours. Baseline intraocular pressure was $25.2\pm3.8$ (mean mm Hg±SEM), $27.2\pm5.5$ mm Hg. At five hours intraocular pressure was $20.6\pm2.0$ mm Hg, and $26.0\pm4.9$ mm Hg; comparing treated and control eyes, respectively. The topical application of a 1% corynanthine solution did not significantly reduce intraocular pressure. The five percent solution did not significantly ($p<0.50$) reduce intraocular pressure when treated and control eyes were compared. Comparing each eye to its baseline intraocular pressure, 5% corynanthine significantly ($p<0.05$) reduced intraocular pressure in the treated eyes from four to eight hours after application, and from six to seven hours in the control eyes. Anterior chamber depth was not significantly ($p<0.30$) reduced using the 1% or 2% solution. The 5% solution caused a significant ($p<0.05$) decrease in anterior chamber depth at three, four and seven hours. Pupil size was not significantly ($p<0.20$) altered by using the 1%, 2% or 5% solutions.

Blood pressure was not significantly ($p<0.40$) reduced using the 2% solution; and was significantly ($p<0.02$) reduced using the 5% solution at one, four and five hours. Pulse rate was not significantly ($p<0.40$) reduced using the 2% solution; and not significantly ($p<0.10$) reduced using the 5% solution.

It is believed that a concentration of about 2%–5% corynanthine tartrate may be the most beneficial for clinical use in patients with glaucoma. The 2% solution is believed to be the optimal concentration for clinical use in treating ocular hypertensives. The 2% solution does not affect anterior chamber depth, pupil size, blood pressure or pulse rate. None of the patients encountered any side effects at any of the concentrations used.

The results set forth in Examples 1–6 demonstrate that corynanthine reduces intraocular pressure in rabbits, monkeys, and humans. Corynanthine does not substantially alter outflow facility or directly measured aqueous humor flow rates. It is believed that corynanthine an $\alpha_1$ adrenergic antagonist may reduce intraocular pressure by increasing uveoscleral outflow.

We claim:

1. A method of reducing intraocular pressure in mammals which comprises applying topically to the eye corynanthine or a pharmaceutically acceptable salt thereof in an amount effective to reduce intraocular pressure.

2. A method of reducing intraocular pressure as described in claim 1 wherein the salt is corynanthine tartrate.

3. A method of treating glaucoma in mammals which comprises applying topically to the eye corynanthine or a pharmaceutically acceptable salt thereof in an amount effective to reduce intraocular pressure.

4. A method of treating glaucoma as described in claim 3 wherein the salt is corynanthine tartrate.

5. A method of treating glaucoma as described in claim 4 wherein the corynanthine tartrate is applied topically as an aqueous solution containing about 2-5% by weight corynanthine tartrate.

6. A method of reducing intraocular pressure as described in claim 2 wherein the corynanthine tartrate is applied topically as an aqueous solution containing about 2-5% by weight corynanthine tartrate.

* * * * *